(12) United States Patent
Schaffer et al.

(10) Patent No.: US 8,494,871 B2
(45) Date of Patent: Jul. 23, 2013

(54) DECISION SUPPORT SYSTEM FOR ACUTE DYNAMIC DISEASES

(75) Inventors: James David Schaffer, Wappingers Falls, NY (US); Mark R. Simpson, White Plains, NY (US); Nicolas Wadih Chbat, White Plain, NY (US); Nilanjana Banerjee, Armonk, NY (US); Yasser H. Alsafadi, Yorktown Heights, NY (US)

(73) Assignee: Koninklijke Philips N.V., Eindhoven (NL)

( * ) Notice: Subject to any disclaimer, the term of this patent is extended or adjusted under 35 U.S.C. 154(b) by 115 days.

(21) Appl. No.: 12/668,431

(22) PCT Filed: Jul. 11, 2008

(86) PCT No.: PCT/IB2008/052800
§ 371 (c)(1),
(2), (4) Date: May 20, 2010

(87) PCT Pub. No.: WO2009/010907
PCT Pub. Date: Jan. 22, 2009

(65) Prior Publication Data
US 2010/0256457 A1    Oct. 7, 2010

Related U.S. Application Data

(60) Provisional application No. 60/949,652, filed on Jul. 13, 2007.

(51) Int. Cl.
*G06Q 10/00* (2006.01)
(52) U.S. Cl.
USPC .................................................. 705/2; 705/3

(58) Field of Classification Search
USPC ............................................................ 705/2
See application file for complete search history.

(56) References Cited

U.S. PATENT DOCUMENTS

2003/0097220 A1    5/2003    Agur et al.
2003/0101076 A1    5/2003    Zaleski
(Continued)

FOREIGN PATENT DOCUMENTS

WO          03021257 A1    3/2003
WO       2007054841 A1    5/2007

OTHER PUBLICATIONS

Rukmini Kumar, Gilles Clermont, Yoram Vodovotz, Carson C. Chow; The dynamic of acute inflammation, Apr. 13, 2004, Journal of theoretical biology 230 (2004) 145-155, www.sciencedirect.com, www.elsevier.com/locate/yjtbi.*

(Continued)

*Primary Examiner* — Hiep V Nguyen

(57) ABSTRACT

A medical apparatus (901, 100) assists clinicians, nurses or other users in choosing an intervention for the treatment of a patent suffering from an acute dynamic disease, e.g. sepsis. The medical apparatus is based on a method where a model of the disease is adapted or personalized to the patient. To ensure that the apparatus remains capable of predicting the health of the patient, the apparatus is continuously provided with new, more recent patient values and the model is continuously adapted to the new patient values. Since the medical apparatus is configured to be continuously adapted to current state of health, the apparatus is able to assist the user by generating disease management information, e.g. suggestions for medications, to an output device (902, 104).

20 Claims, 14 Drawing Sheets

U.S. PATENT DOCUMENTS

2003/0194752 A1   10/2003   Anderson et al.
2004/0096917 A1   5/2004    Ivey et al.
2004/0106142 A1   6/2004    Ivey et al.
2008/0281170 A1*  11/2008   Eshelman et al. ............ 600/301

OTHER PUBLICATIONS

Angela Reynolds, Jonathan Rubin, Gille Clermont, Judy Day: I. Derivation of model and analysis of anti-inflammation, Feb. 22, 2006, Journal of Theoretical biology 242 (2006) 220-236, www.sciencedirect.com, www.elsevier.com/locate/yjtbi.*

Beneken, J.E.W., et al.; Prognosis, Trend and Prediction in Patient Management; 1979; J. of Biomedical Engineering; 1(3)185-200.

Brause, R.; Adaptive Modeling of Biochemical Pathways; 2003; IEEE Int'l Conf. on Tools with Artificial Intelligence; vol. Conf. 15; pp. 62-68.

Tung Fischer; Unterstutzung im Kampf gegen schwere Sepsis; 2007; Krankenhaushygiene + Infektionsverh; 29(3) 106-112.

Kumar, R., et al.; The dynamics of acute inflammation; 2004; J. of Theoretical Biology; 230:145-155.

Pilz, G., et al.; A Basic program for calculation of APACHE II and Elebute scores and sepsis evaluation in intensive care medicine; 1991; Computers in Biology and Medicine; 21(3)abstract.

Reynolds, A., et al.; A reduced mathematical model of the acute inflammatory response: I. Derivation of model and analysis of anti-inflammation; 2006; J. of Theoretical Biology; 242:220-236.

Vodovotz, Y., et al.; Evidence-based modeling of critical illness: an initial consensus from the Society for complexity in Acute Illness; 2007; J. of Critical Care; 22(1)77-84.

* cited by examiner

A method for assisting a clinician in

DECISION SUPPORT SYSTEM FOR ACUTE DYNAMIC DISEASES

FIELD OF THE INVENTION

The invention relates to a method for assisting a clinician in treating patients, in particular patient suffering from acute dynamics diseases.

BACKGROUND OF THE INVENTION

Sepsis is a severe disease for example in the form of a malady of the immune system caused by an infection or other traumas.

If the patient suffering from sepsis is not treated or if the therapy is not optimal the patient may die.

Sepsis is a complicated disease involving the reactions of several components of the immune system to an infection. These reactions are difficult to monitor because they involve many cell types all communicating with each other via chemical messengers that are not routinely measured in the clinic and even if they were, these measurements would be difficult to interpret because the dynamics of these responses are so complex and vary widely among patients. The complexity of sepsis may be seen by the facts that sepsis is the tenth leading cause of death in the USA and the leading cause of death in non-cardiac intensive care units in spite of several decades of research.

Today therapies of sepsis are based on the clinicians experience and skills, however, due to the complexity of sepsis even experienced clinicians may not be able to execute the optimal therapy, or the clinician may even execute a therapy leading to a deteriorated situation for the patient.

Some of the challenges faced by the clinicians when a sepsis patient needs treatment are caused by the large number of unknown biological and physiological factors affecting the development of the disease as well as the dynamic and often rapid changing behaviour of the disease.

Accordingly, it may be seen as a problem to create a system capable of assisting the clinician in executing a suitable therapy for patients suffering from diseases such as sepsis.

US 2003/0097220 discloses a decision support system for recommending an optimal treatment protocol for a specific individual. The system comprises generally a system model, a plurality of treatment protocols, a system model modifier, wherein said system model is modified by the system model modifier based on parameters specific to the individual; and a selector to select an optimal treatment protocol from said plurality of treatment protocols based on the modified system model.

The method disclosed in US 2003/0097220 is related to treating cancer and, therefore, is not capable of dealing with diseases having a highly dynamic nature of development that change rapidly in short time scales (e.g. hours) and, consequently, is not suitable for assisting a clinician in treating sepsis.

SUMMARY OF THE INVENTION

Accordingly, the invention preferably seeks to mitigate, alleviate or eliminate one or more of the above mentioned problems singly or in any combination. In particular, it may be seen as an object of the present invention to provide a method and an apparatus capable of modelling acute dynamic diseases and predicting future patient values for assisting the clinician in managing the disease.

This object and several other objects are obtained in a first aspect of the invention by providing a method according to the independent claim.

The invention is particularly, but not exclusively, advantageous for predicting patient values of a patient with an acute dynamic disease and outputting disease management information derived from the predicted patient values for assisting the clinician in managing the disease.

Accordingly, in an embodiment of the first aspect of the invention the method comprises adapting a mathematical model to the initial patient values. That is, a plurality of patient values obtained from measurements of biological and/or physiological parameters of the patient are used to adapt or personalise the model to the patient or more precisely to the disease of the patient. Since the clinical condition of the patient is likely to change, e.g. due to the development of the disease, it may be necessary or beneficial to perform a new adaption of the model to more recent patient values so that the model is better suited for predicting future patient values. Thus, by continuing adapting the model to the dynamic of the patient using recent patient values and using a plurality of the initial patient values, the model is tuned to the most recent state of the health of the patient. An advantage of continuously adapting the model may be that the model is capable of predicting future patient values even when the acute dynamic disease exhibits highly dynamic changes of various patient values. Thus, by continuously determining predicted patient values, disease management information can be outputted to the output device of the medical apparatus for assisting a clinician in managing the acute dynamic disease. That is, the disease management information may provide the clinician with guidance for executing a particular intervention.

It may be an advantage of the first aspect of the invention that the model is initially adapted to initial patient values since this may provide the possibility to make a first prediction of patient values. The first prediction of patient values may be outputted via the output device allowing the clinician to make a first quick assessment of the health of the patient. It may be another advantage of the first aspect of the invention that the method is tolerant to missing patient values since the model is adapted to use a plurality of patient values and, therefore, the method will continue to provide reasonable predictions of future patient values even if some patient values provided to the medial apparatus were late.

It may be an other advantage that the method, according to the first aspect, may combine a mathematical model of the immune system dynamics with serial measurements of key chemical messengers and algorithms capable of tuning the model to the individual patient and presenting to clinicians information displays that shows disease management information, for example the patient's current state and/or and its probably future course.

According to another aspect, the disease management information comprises an intervention. The one or more interventions may be provided to the user or clinician as a suggestion to medication regimes or interventions, for example in the form of a list of possible interventions or as a graphical illustration of possible interventions. The suggested interventions may have been determined by analysing the predicted patient values.

According to another aspect, the disease management information comprises timing data for executing the intervention to the output device. Thus, it may be an advantage to output a time for initiating a medication since this may improve the therapeutic effect of the medication. It may be another advantage that the clinician is assisted to initiate a medication at an optimum time. The timing data may have been determined by analysing the predicted patient values.

According to another aspect, the disease management information comprises estimates of confidence of the predicted patient values. Accordingly, it may be an advantage to provide estimates of confidence of predictions since it may allow the clinician to judge the tolerances of the estimated patient values, for example the timing of the onset and peak of a hyper-inflammation.

According to another aspect, the medical apparatus is adapted for receiving therapy values of interventions. The therapy values may be provided via the input device or the clinician may provide values manually to the medical apparatus via the user input. By using the therapy values the predicted patient values may be determined by applying these therapy values in the model. The therapy values may comprise values of medication for example a serum antibiotic level, a serum anti-inflammation level or levels of other medications. Alternatively or additionally, the therapy values may comprise values of a medication dose regimen generator, for example the amplitude of the medication dose, the period between medications, the duty cycle of medication, i.e. the percent of the period during which medication is administered, the time for initiating the medication regimen and/or the time for finishing the medication regimen. It may be an advantage using therapy values in the model since the predicted future patient values include the therapeutic effect of a medication which has already been executed. Alternatively or additionally, it may be an advantage using therapy values in the model since this may provide a possibility of testing different medications, so that the clinician is able to select a particular medication with a favourable outcome for the patient. Thus, it may be an advantage to offer clinicians a capability to explore the likely disease course under various therapeutic strategies of the clinician's own devising, making it possible for clinicians to exploit knowledge of circumstances that may not be known to the system (e.g. comorbidities).

According to another aspect, the computing device is used to determine the next sample time for providing the medical apparatus with new patient values, which may be determined using the initial and recent patient values in connection with the model. The determined time for providing new patient values may be outputted to the output device for assisting the clinician when to take new biological and/or physiological samples of the patient so as to provide the medical apparatus with recent patient values via the input device or the user input device.

According to another aspect, the sample time is determined from previous patient values by analysing the dynamics of the patient values, for example calculating the frequency content using a FFT analyser or the rate of change of patient values. Thus, if the recent patient values show stable conditions of the patient, for example showing low frequency content or low rate of changes, the next time for providing the medical apparatus with new patient values may be postponed or new patient values may not need to be provided at all unless the clinicians observe a change in the patient state. If the recent patient values show un-stable conditions of the patient, for example showing high frequency content or high rate of changes, the next time for providing the medical apparatus with new patient values may be expedited to improve the accuracy of predicted patient values.

According to another aspect, the sample time is periodic with a fixed frequency. The frequency may be determined from the dynamics of the patient values. The periodicity of the sample time may be less than 10 hours, preferably less than 5 hours, more preferably less than 2 hours, for example less than 1 hour.

According to another aspect, health regions of distinguishing health outcomes in model space are determined by providing the adapted model with patient data for prediction of health outcomes. It may be an advantage to determine health regions, since the health regions may provide an advantageous method for analysing patient data and for determining possible interventions.

According to another aspect, patient trajectories of various patient health outcomes are determined in model space. It may be an advantage to determine patient trajectories since patient trajectories may provide the clinician with an easy understandable graphical presentation of the health of the patent, the effect of interventions, and the future development of the patient values.

According to another aspect, the output device is adapted for showing disease management information, for example patient trajectories, health regions and interventions, for assisting the clinician.

The aspects may each be combined with any of the other aspects. These and other aspects will be apparent from and elucidated with reference to the embodiments described hereinafter.

In summary, the present invention relates in an embodiment to a medical apparatus for assisting clinicians, nurses or other users in choosing an intervention for the treatment of a patent suffering from an acute dynamic disease, e.g. sepsis. The medical apparatus is based on a method where a model of the disease is adapted or personalised to the patient. To ensure that the apparatus remains capable of predicting the health of the patient, the apparatus is continuously provided with new patient values and the model is continuously adapted to the new patient values. Since the medical apparatus is configured to be continuously adapted to current state of health, the apparatus is able to assist the user by generating disease management information, e.g. suggestions for medications, to an output device.

BRIEF DESCRIPTION OF THE FIGURES

The present invention will now be explained, by way of example only, with reference to the accompanying Figures, where.

DETAILED DESCRIPTION OF AN EMBODIMENT

Figure 1:
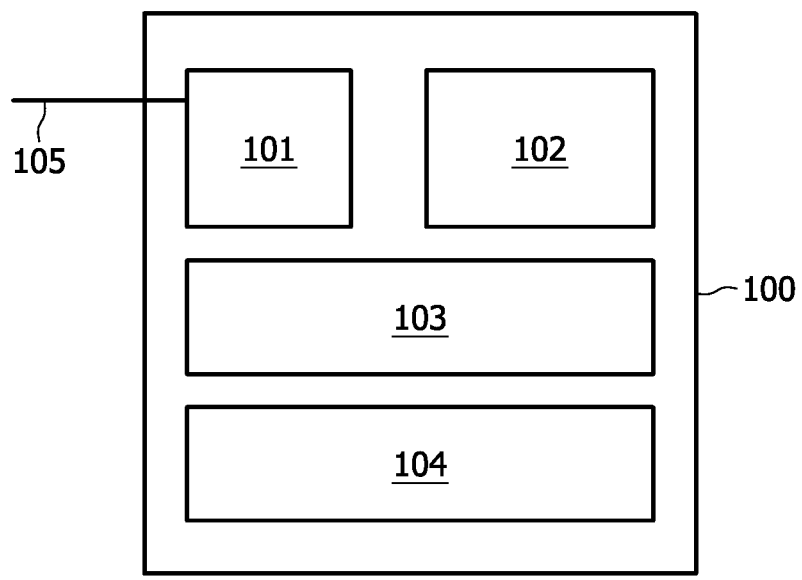
FIG. 1 shows a medical apparatus 100 for assisting the clinician in managing an acute dynamic illness.

An embodiment of this invention relates to diseases categorised as inflammatory diseases or dynamic diseases of the immune system, for example sepsis. Such severe diseases have a highly dynamic nature, that is, such diseases often develop dynamically implying that the onset and course of the disease are difficult to predict. Furthermore, these diseases develop rapidly in a short time scale. An intervention is beneficial in a short window otherwise a very unfavourable outcome (e.g., death) may occur. When the clinician is not able to deal with the large number of factors affecting the disease, which is likely to be the case in the clinic, the clinician may be able to choose a more optimal therapy by using a medical apparatus capable of analysing a large number of patient values for assisting the clinician in therapy choices.

Within the context of this description the term intervention is to be understood as meaning any kind of interventions, such as interventions, diagnostic interventions, administrative interventions, or palliative intervention.

Within the context of this description the term clinician is to be understood as equivalently referring to a care giver, a healthcare person, a physician, a nurse, a technician, or a hospital administrator.

The immune system is a multiply redundant control system that has evolved to be very robust. Sepsis is a complicated disease involving the reactions of several components of the immune system to an infection. These reactions are difficult to monitor because they involve many cell types all communicating with each other via chemical messengers that are not routinely measured in the clinic and even if they were, these measurements would be difficult to interpret because the dynamics of these responses are so complex and vary widely among patients. This makes the clinical management of sepsis episodes very difficult where it is recognized that no one therapeutic approach is optimal for all patients; an inadequate immune response may call for antibiotic treatment while an overreaction by the immune system may call for anti-inflammatory and/or anticoagulant therapies and the timing of interventions is known to be critical, but very difficult to judge correctly.

As mentioned an embodiment of this invention relates to sepsis. However, the invention is not limited to sepsis, inflammatory diseases or dynamic diseases of the immune system since embodiments of the invention may also be applicable to other diseases, for example auto-immune disorders like arthritis, and the inflammatory component of cancer or heart diseases. In general embodiments of the invention may be applicable to various diseases within the group of acute dynamic diseases which cover the diseases mentioned in this description and other diseases as well. Other examples of acute dynamic diseases are fibrillation of the heart where the normal pace-making dynamic goes wrong and epileptic seizures where the normal coordination of neural firings goes wrong.

An embodiment of the invention is related a group of diseases referred to as acute dynamic diseases. Acute dynamic diseases comprise those diseases where the essence of the disease is a malfunction of a biological dynamic where none of the biological mechanisms is diseased or corrupted. Accordingly, some acute dynamic diseases can be seen as a disorder in the biological dynamics of the immune system. The treatment of acute dynamic diseases can be seen as resetting the biological dynamics or bringing biological dynamics on track again.

When the specific term sepsis is used in a context, this context should not be understood as limited to sepsis, but should be understood broadly as inflammatory diseases, dynamic diseases of the immune system or acute dynamic diseases in that context. Accordingly, reference to sepsis may be used for convenience where the actual context is equally valid for other diseases within larger group of acute dynamic diseases, or the smaller group of inflammatory diseases or dynamic diseases of the immune system.

In contrast to acute dynamic diseases, for example cancer is a disease caused by corrupted genes. Thus, the course of a cancer disease is very different than acute dynamic diseases since cancer develops over a much longer scale (weeks, months or even years), cancer does not exhibit a dynamic nature but a more monotone nature and, thereby, cancer is easier to predict—at least over a short term such as weeks.

Thus, in cancer, the tumor cells are corrupted versions of what used to be normal self cells—the therapeutic goal is to eliminate them. In an acute dynamic disease, there isn't necessarily anything wrong with any of the immune system's cells, so the therapy goal would not be to kill any of them. Of course pathogen cells (infectious cells) should be killed if the immune system can't do that for itself. The disease is that the ensemble behaviour of these cells starts to deviate from the healthy response that normally returns the body to homeostasis (a stable condition of the body). So the therapeutic goal is to somehow modify the signalling among these cells to restore the healthy control dynamics. This is difficult because this system has been evolved to be robust; it's multiply redundant—hence the many failures of single drugs designed to do this.

Acute dynamic diseases typically can be categorised by a dynamic nature involving fast changes in various health data or patient values, e.g. the level of pathogens and various types of leukocytes. For example, the time constants describing the dynamics of inflammation are clearly different than the time constants of a cancer disease, since the dynamics of inflammation may unfold in minutes to hours, and whereas seizures and fibrillations (particular acute dynamic diseases) of course unfold in seconds to minutes. Accordingly, health data related to acute dynamic diseases may change significantly within hours, such as within 4 hours, within 2 hours or even within 1 hour. However, health data related to particular inflammatory diseases may change even faster for example within one hour, within minutes, such as between 1 to 30 minutes or even within seconds, such as within 1 to 30 seconds.

Similarly, acute dynamic diseases may develop into a fatal state causing death within hours, such as within 4 hours, within 2 hours or even within 1 hour. A heart attack caused by an acute dynamic disease can be fatal in a few minutes, such as between 1 to 5 minutes.

Thus, the fast developing courses of acute dynamics diseases set particular requirements to the capability of medical assisting apparatuses of tracking and predicting the courses of such diseases which are distinct from similar apparatuses for other diseases, for example cancer diseases.

FIG. 1 shows a medical apparatus 100 for assisting the clinician in managing an acute dynamic disease for example by assisting the clinician in selecting an appropriate therapy. The medical apparatus may equivalently be referred to as a clinical decision support system. The medical apparatus 100 comprises an input device 101 for receiving patient values characterising biological and/or physiological measures of the patient and for receiving therapy data characterising measures of therapies or medications.

Biological values refer for example to measurements of blood samples where the presence or quantity of particular biological substances or biomolecules are determined using various medical devices, for example assays. Such biological values comprise for example cytokines, coagulation factors and reactive oxygen species and pathogens.

Physical values comprise values obtained from measurements of for example body temperature, blood pressure, heart rate, respiration rate and possibly count of various kinds of white blood cells (leukocytes).

The biological and physical values may be provided to the input device 101 via connections 105 to some external medical devices or assays.

The medical apparatus 100 may in an embodiment further comprise a user input device 102, where the user of the medical apparatus, eg the clinician, is able to provide the medical apparatus 100 with other patient values. For example the clinician may input patient values that are not provided via connections 105. Via the user input device 102 the clinician may also input therapy data or values. Therapy data comprises data or values of for example medications or drugs that have been given or will be given soon. Also therapy data may be inputted as test data for testing the therapeutic effect of the possible therapy. The user input device 102 may be a keyboard or a touchpad.

The therapy data could be type, dosage and frequency of dosage for example of an antibiotic.

The medical apparatus 100 further comprises a computing device 103 capable of processing the patient data and treatment data provided from the input device 101 and/or the user input device 102. The computing device is adapted to process the biological and physical values obtained via connections 105 as well as biological, physical and therapeutic values obtained via or the user input device 102. The processing of data is carried out using a model of a disease so that the development of the patient's disease can be predicted.

The medical apparatus 100 additionally comprises an output device 104, for example a graphical user interface 104 for assisting the clinician in understanding the development of the disease and for assisting the clinician in selecting a successful intervention. For that purpose various data from the computing device are provided to the output device 104, where the output device is adapted for presenting data in a form that is useful and easily comprehensible for the clinician.

The input device 101, the user input device 102, the computing device 103 and the output device 104 may be separate devices interconnected. Alternatively, one or more of the mentioned devices (101-104) may be combined. For example the user input device 102 and the output device may be combined as a single device. The computing device 103 may be a computer adapted to execute program code constituting the model of the disease and to process input values from the input device 101 and user input device 102 using the model. Additionally, the computing device 103 may be configured for adapting the model to the patient values and for determining some advisable therapies. The output device 104 and/or user input device 102 may be comprised for example by a computer and a monitor.

The input device 101, the user input device 102 and the output device 104 may be an electronic device e.g. a printed circuit board connectable or integrated with the computing device 103. The user input device 102 and the output device 104 may be connected to monitors for providing a signal representing values or data to the monitor for displaying such values or data.

As will be apparent in the following, a condition for medical apparatus to be capable of assisting the clinician in treating the sepsis patient is that the medical apparatus is capable of predicting the development of the patient's sepsis. In order to provide accurate predictions of the disease, it may be important that the medical apparatus 100 is provided with all biological and physical values that are relevant for the model at a given stage of disease, and that the values are provided at a sufficient high frequency. At the same time it is also important the patient is not exposed to too many sample-takings, eg blood samples, since the patient may be in a critical state and since blood sampling can expose patient to additional risk of new infection. Also, it may be desirable to reduce the cost for assays used for taking biological measurements.

As will also be apparent in the following, it may be important that a particular medical intervention is executed at a particular time or within a particular period of time. Accordingly, timing is an important issue both in regard to providing patient values to the medical apparatus 100, and with regard the determining the timing of executing a therapy.

Furthermore, since sepsis may develop differently from patient to patient it is important that the medical apparatus is capable of adapting or personalising the model to the patient and, furthermore, since the behaviour of sepsis may change within hours or even minutes, it may be important that the model can be re-adapted to the current state of sepsis by use of recent patient data.

As stated above, it is important the model is capable of capturing the essential dynamics and timing of the immune response to infection in order to accurately model diseases, for example sepsis. The following 3-variable model disclosed in "R. Kumar, G. Clermont, Y. Vodovotz, C. C. Chow, *The dynamics of acute inflammation*, The Journal of Theoretical Biology, 2004.04.044, 145-155." hereby incorporated by reference, exhibits, depending on initial conditions and parameter values, a variety of disease dynamics that have been observed in the clinic. This relatively simple model only includes biological, biomolecular or cellular dynamics and does not include physiological patient data. The model consists of the following three ordinary differential equations:

$$dp/dt = k_p p(1-p) - k_{pm} mp \quad (1) \text{ pathogen (p)}$$

$$dm/dt = (k_{mp} p + l) m(1-m) - m \quad (2) \text{ early pro-inflammatories (m)}$$

$$dl/dt = k_{lm} f(m) - k_l l \quad (3) \text{ late pro-inflammatories (l)}$$

where $$f(m) = 1 + \tanh\left(\frac{m - \theta}{w}\right)$$

and hereafter we let $\theta = 1.0$ and $w = 0.5$.

The model state variables are: p for the population level of the pathogen responsible for the immune response and the sepsis, m for the early pro-inflammatory response (e.g. the level of serum cytokines and macrophages) and, l for the late pro-inflammatory response. Here, the pathogen (p) is the infectious agent comprising for example viruses, bacteria, fungi or parasites. Thus, measurements of pathogens may provide information of the development of the disease.

In addition to the three state variables, there are five rate constants, the k's. These parameters are rate constants where $k_{ij}$ indicates the rate at which the rate-of-change of variable i is influenced by the level of variable j; $k_i$ is the rate at which the rate-of-change of variable i is influenced by its own level. One additional modification of the model is applied: if the pathogen variable drops below a threshold (e.g. 0.0005), the above equations are neglected and the pathogen is declared eliminated. Without this modification, unrealistic returns of pathogen populations whose numbers had dropped below a level that would represent less than a single cell would be observed and might result in erroneous data from the computing device 103.

The table below shows the five different dynamics exhibited by the model. These dynamics have all been observed in the clinic.

TABLE 1

| Initial conditions | | | parameters | | | | | |
|---|---|---|---|---|---|---|---|---|
| p(0) | m(0) | l(0) | $k_P$ | $k_{pm}$ | $k_{mp}$ | $k_{lm}$ | $k_l$ | dynamics |
| 0.01 | 0.05 | 0.539 | 3 | 30 | 25 | 15 | 1 | healthy response |
| 0.20 | 0.05 | 0.539 | 3 | 30 | 25 | 15 | 1 | Persistent non-infectious inflammation |
| 0.01 | 0.05 | 0.539 | 3 | 3 | 25 | 15 | 1 | Persistent infectious inflammation |
| 0.01 | 0.05 | 0.179 | 3 | 30 | 25 | 5 | 1 | Recurrent infection |
| 0.01 | 0.05 | 0.539 | 3 | 30 | 0.4 | 15 | 1 | Severe immuno-deficiency |

Figure 2A:
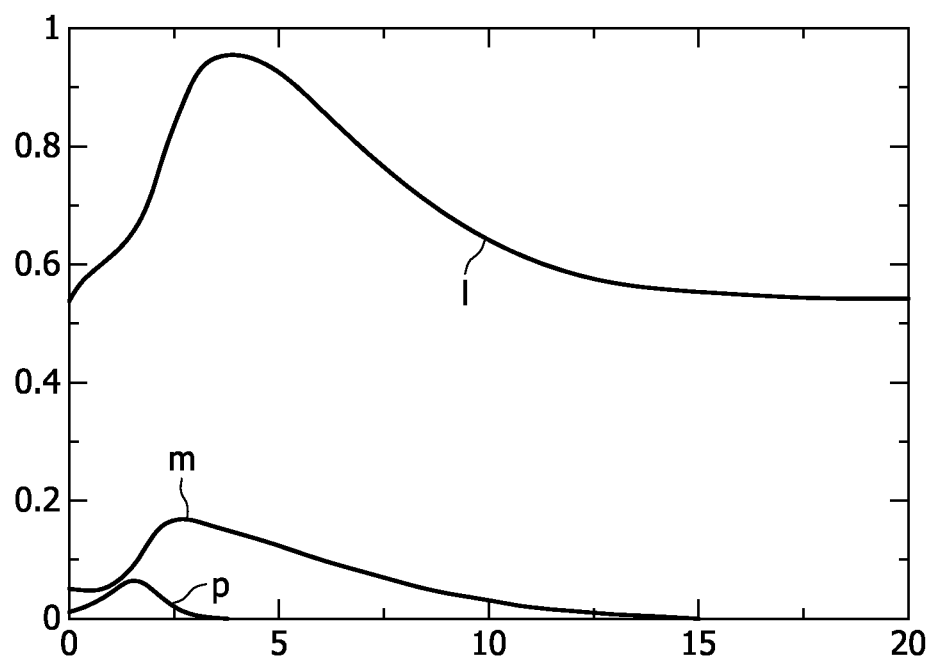
FIG. 2A-E shows time courses corresponding to five dynamics of the health of a patient.
Figure 2B:
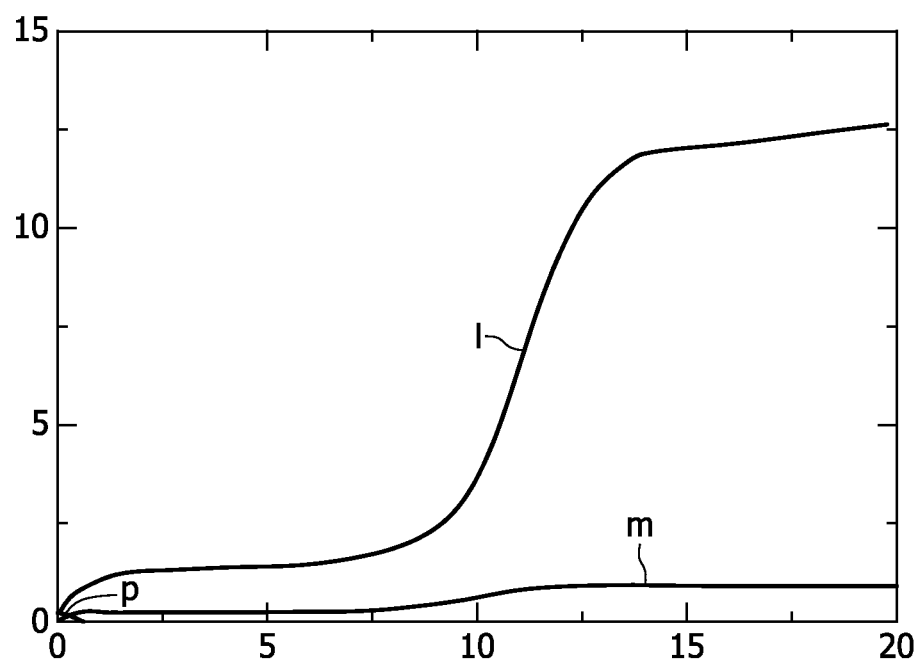
Figure 2C:
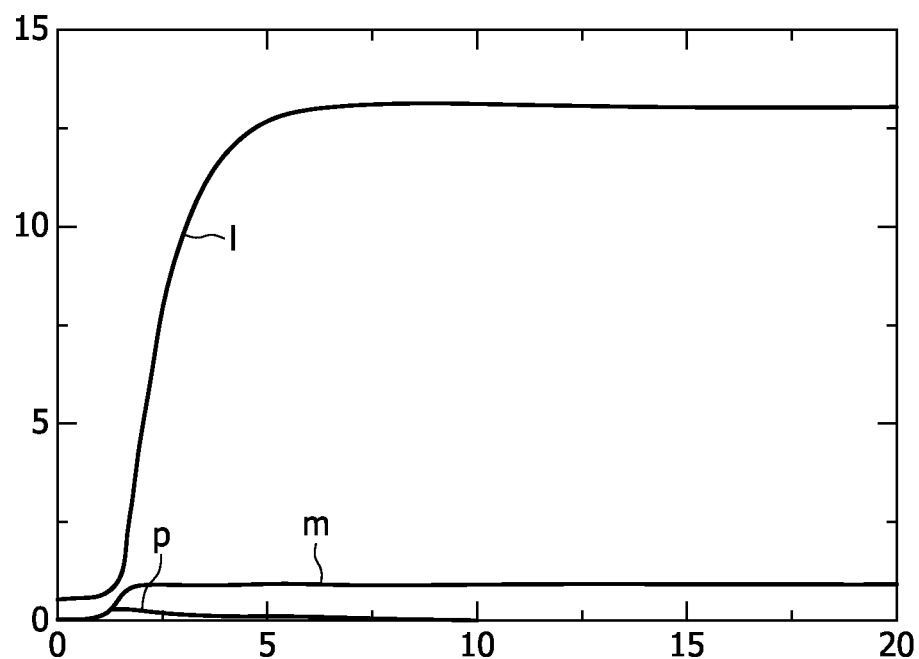
Figure 2D:
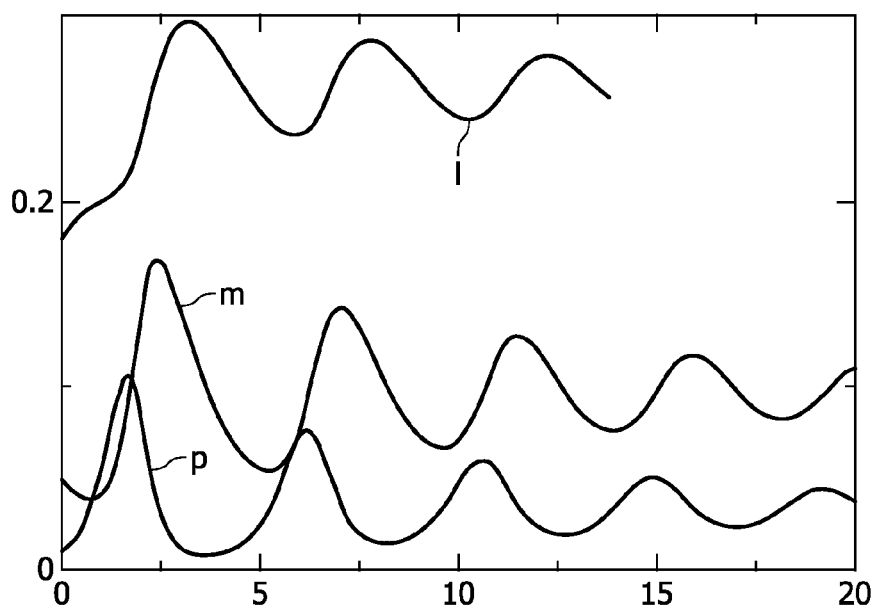
Figure 2E:
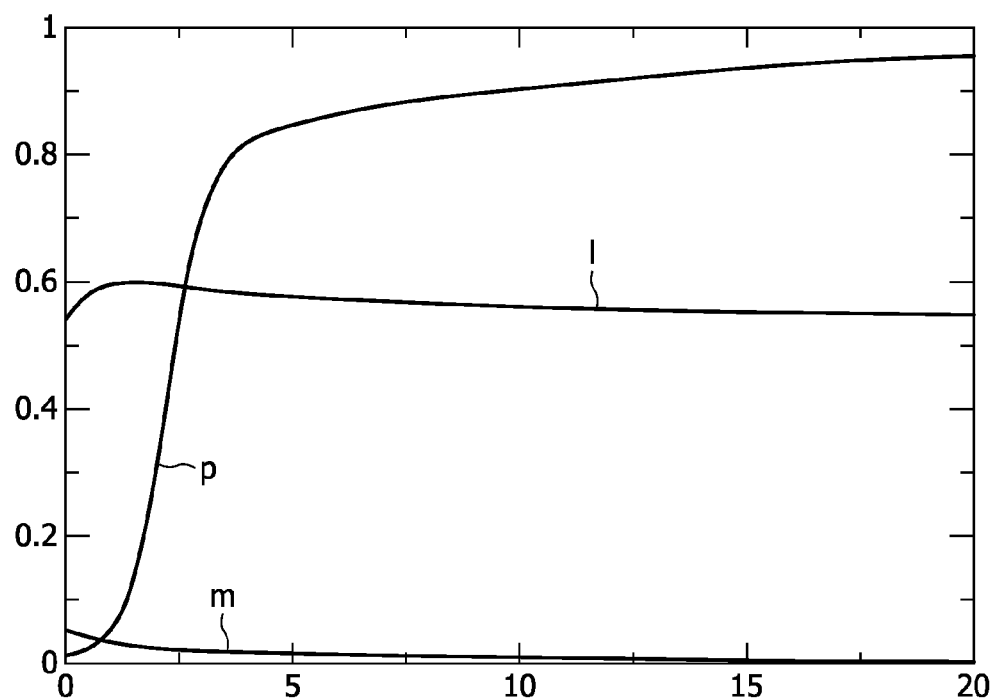

These time courses corresponding to five dynamics indicated in the above table are shown in FIGS. 2A-E. The abscissa represent time in hours and the ordinate represent levels of pathogens (p), early inflammatory response (m) and late inflammatory response (l) corresponding to the curves of the dynamics. Thus, FIG. 2A shows dynamics of a healthy response, FIG. 2B shows persistent non-infectious inflammation, FIG. 2C shows persistent infectious inflammation, FIG. 2D shows recurrent infection and FIG. 2E shows severe immuno-deficiency.

Equations 1-3 may be solved by any suitable mathematical method by providing the model with patient values.

As an example of showing the importance of providing the medical apparatus 100 and the model with a sufficient number of patient data and with a sufficient frequency, the patient data p, m and l from FIG. 2A are used to estimate the k-parameters of equations 1-3 by providing the model with samples of patient data p, m and l from FIG. 2A. The k-parameters can be estimated using a least-squares method or similar minimisation/optimisation/estimation methods known to the skilled person for calculating those k-values providing the best fit of the patient data to the model. Accordingly, the estimation of k-parameters corresponds to adapting the model to the patient values.

Thus, the dynamics of p, m and l in FIG. 2A may be seen as the dynamics of real patient data of a real patient. In the first example, the k parameters shown in table 2 below are estimated on basis of a total of 9 samples collected by sampling the patient data from FIG. 2A at 2 samples per hour. Thus, table 2 shows the true parameters from FIG. 2A and the estimated parameters.

TABLE 2

| | true | estimate |
|---|---|---|
| $k_p$ | 3 | 2.9969 |
| $k_{pm}$ | 30 | 26.8104 |
| $k_{mp}$ | 25 | 27.2420 |
| $k_{lm}$ | 15 | 15.2493 |
| $k_l$ | 1 | 1.0336 |

Figure 3:
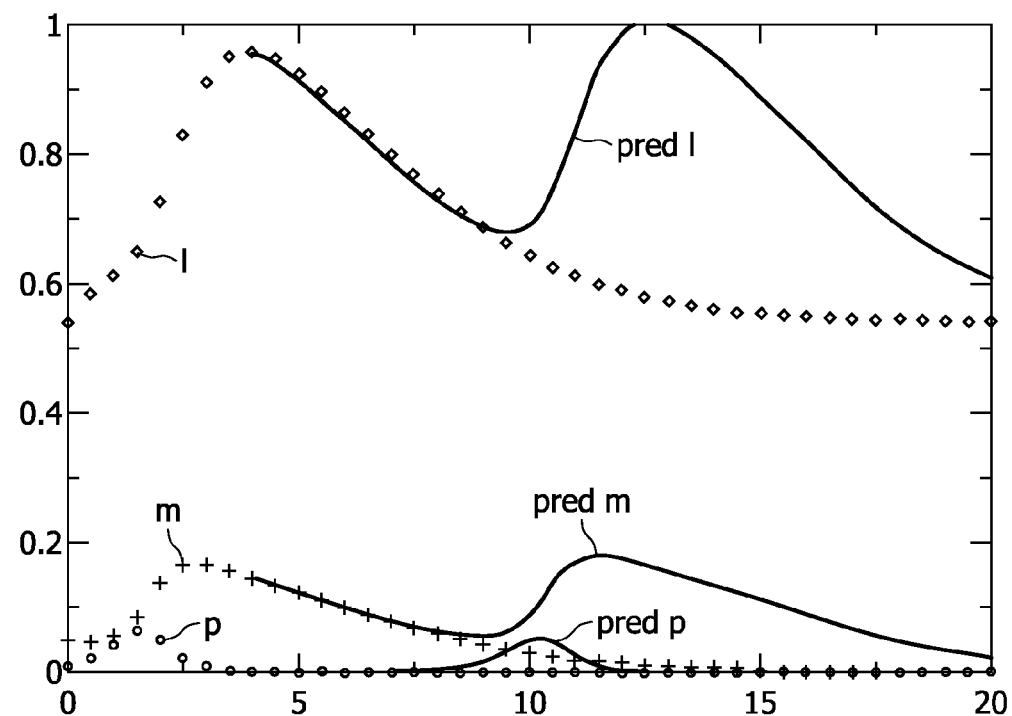
FIG. 3 shows patient data compared with predicted patient dynamics.

FIG. 3 shows patient values (p, l, m) from FIG. 2A compared with predicted patient dynamics (Xp, Xl, Xm). FIG. 3 shows that the predictions for the near future are good, but that an obvious deviation occurs starting at about hour 9, about 5 hours following the last observation.

The predicted patient values (Xp, Xl, Xm) are determined by providing the medical apparatus 100 with initial patient values. Initial patient values comprise one or more values or set of values of patient values (p, l, m) indicated with dots in FIG. 3. The model is then adapted to the initial one or more values or set of values of initial patient values (p, l, m). In order to continuously adapting the model to the current health of the patent, the medical apparatus 100 is provided with new recent patient values (p, l, m) which in combination with one or more of the initial patient values are used to re-adapt the model. Accordingly, a series of historic patient values and recent patient values are used for continuously adapting the model by continuously adapting the k-parameters.

FIG. 3 illustrates the importance of using a sufficient number of patient values obtained at a sufficient high sampling frequency. Thus, the sampling frequency must be chosen with careful consideration of the fastest expected dynamics of the disease. In the example in FIG. 3, the pathogen (p) was essentially defeated by about hour 3 with the decline of the immune response (l and m) following for some hours after that. Nine samples at half-hourly intervals could capture the bulk of the important dynamics and so the estimates and predictions were good. More complex models contain larger numbers of parameters. Since there are constraints on how frequently blood can be drawn from ill patients and how rapidly the biological or biomolecular measurements can be obtained, it may be an advantage if the medical apparatus can provide the user or the clinician with information about what biological values should be provided to the medical apparatus 100, and how frequently they should be provided, for ensuring accurate prediction of the dynamic development of the disease.

The comparison between predicted patient values and real patient values as shown in FIG. 3 shows the importance of adapting the model to the current health of the patient on basis of the recent patient data. Clearly, the more samples of recent patient data that are available for adapting the model to the historic health data of the patient the more accurate the model becomes. However, since sepsis or other inflammatory diseases may only be diagnosed in a late stage and since inflammatory diseases may develop quickly and change their nature unexpectedly—in view of a clinicians view—it may be an advantage to continuously adapting the model to the current health of the patient on basis of the most recent patient data. In this way not only the nine samples from the example in FIG. 3 is used, but also subsequent samples of patient data are used to continuously updating the model, so that the model is capable of predicting future patient values, even in the case where the disease changes unexpectedly. In that way, the medical apparatus 100 may be capable of predicting unexpected changes in patient values, where eg a clinician may not have been able to predict that unexpected change. Clearly, the capability of assisting the clinician in predicting such unexpected changes would be a great benefit.

Since the model may already have been adapted to the fundamental dynamics of the patient data, in an embodiment the continued adapting of the model to the patient values may be performed at a lower frequency while maintaining a sufficient accuracy of patient predictions. Thus, whereas the first 9 samples were obtained at a frequency of 2 samples per hour, the continued inputting of patient values to the medical apparatus 100 may be performed at a lower frequency. Therefore, in an embodiment, the method for assisting the clinician comprises suggesting the time (ie sample times) for providing the medical apparatus 100 with new patient values obtained from biological/physiological analyses of new samples. The suggested times for providing new patent values may be based on the rate-of-change of specific patient values (p, l, m) or the frequency of dynamics as determined by the computing device 103 eg by using the Eigen values of the model. Alternatively, or additionally, the suggested times for providing new patient values may be based on values inputted to the user input device 102, eg calculated as a compromise between calculated times and times inputted via the user input device 102.

For example, if the measured patient values provided to the input device 101 start approaching the predicted patient values closer and closer, it may be sufficient to provide patient values less frequently since predictions are becoming more accurate. If the patient state is far from a predicted boundary (see FIG. 8, FIG. 9 and accompanying description with regard to predicted boundaries), the final outcome is less uncertain and it is less important to have great accuracy and, therefore, it may suffice to provide patient values less frequently. Conversely, if the patient state is close to the boundary between say life and death, it may be beneficial to provide patient values more frequently. Also, if the measured patient values diverge from the predicted patient values, patient values should be provided to the medical apparatus 100 more frequently as the confidence in the clinical prediction becomes less certain.

The predictions of patient values (as shown in FIG. 3 or other predicted patient values) may be used to assist the clinician by adapting the medical apparatus 100 to provide disease management information determined from the predicted patient values for example by observing that the level of a pathogen is increasing and the expected inflammatory response is not increasing then the health of the patient may be heading towards a particular clinical state (e.g. immune insufficiency) which requires a particular intervention (e.g. medication of a particular antibiotic). Similarly, disease management information may be determined from predicted patient values for example, if the pathogen level is predicted to decline to zero but the inflammatory response is predicted to continue to escalate beyond healthy levels, then the patient may be heading towards a particular clinical state (e.g. hyperinflammation) which requires another particular intervention (e.g. anti-inflammatory drugs).

The predictions of patient values (as shown in FIG. 3 or other predicted patient values) may be used to assist the clinician in understanding how the sepsis will develop, and from this understanding the clinician may be able to decide what intervention should be initiated. However, by extending the model to include the interaction between patient values and drugs of an intervention, the clinician will be able to predict the effect of different intended interventions and, therefore, will be able to choose a particular intervention having the desired outcome.

Such a model which includes interventions in the form of antibiotic therapy and/or anti-inflammatory therapy is given by equations 4-9.

$$dp/dt = k_p p(1-p) - k_{pm} mp - k_{pb} bp/(c_b + b) \quad (4) \text{ pathogen (p)}$$

$$dm/dt = (k_{mp} p + l)m(1-m) - m - k_{mi} im/(c_i + i) \quad (5) \text{ early pro-inflammatories (m)}$$

$$dl/dt = k_{lm} f(m) - k_l l \quad (6) \text{ late pro-inflammatories (l)}$$

$$db/dt = r(t, t_{start\_j}, t_{stop\_j}, \text{period}_b, \text{dose}_b, \text{duty}_b) - k_b b \quad (7) \text{ serum antibiotic level (b)}$$

$$di/dt = r(t, t_{start\_j}, t_{stop\_j}, \text{period}_i, \text{dose}_i, \text{duty}_i) - k_i i \quad (8) \text{ serum anti-inflammation (i)}$$

where:

$$r(t, t_{start}, t_{stop}, \text{period}, \text{dose}, \text{duty}) \quad (9) \text{ dose regimen generator}$$

is a function that permits a wide range of dosing regimens.

Figure 4:
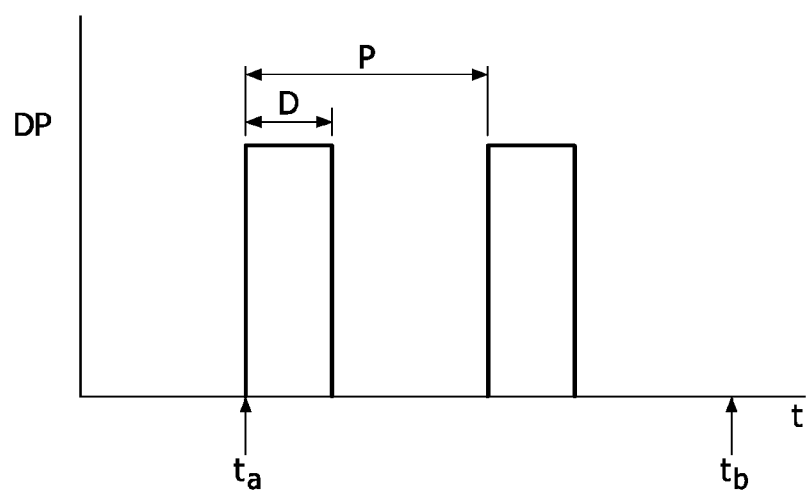
FIG. 4 shows the function r of a dose regimen generator.

The function r may in an example be a square wave generator with a period of period hours, an amplitude of dose (DP, FIG. 4), and where duty (D) is the percent of the period during which medication is administered. The entire regimen is restricted to the time interval from $t_a$ to $t_b$. The parameter period (P) may be interpreted to mean "a dose every period hour." The parameters $c_b$ and $c_i$ are part of the pharmacokynetics and, like $k_{pb}$, $k_b$, $k_{mi}$, and $k_i$, are considered as known properties of the selected drugs. The function r of the dose regimen generator is shown in FIG. 4.

Thus, the medical apparatus can be provided with therapy values, eg one or more of the parameters: b, i, dose, period, duty, ta, tb. The values may be provided by configuring the user input device 102 so that the clinician can input therapy values manually. Additionally, or alternatively, therapy values may be provided from apparatuses via connection 105.

The mentioned list of therapy values should not be understood as an exclusive list that is, other therapy values are equally applicable. The many therapies available to clinicians include agents aimed at specific pathways in the immune system response including coagulation and arachidonic acid pathways, specific endotoxins (e.g. LPS), pro- and anti-inflammation pathways, antioxidants and others.

Figure 5A:
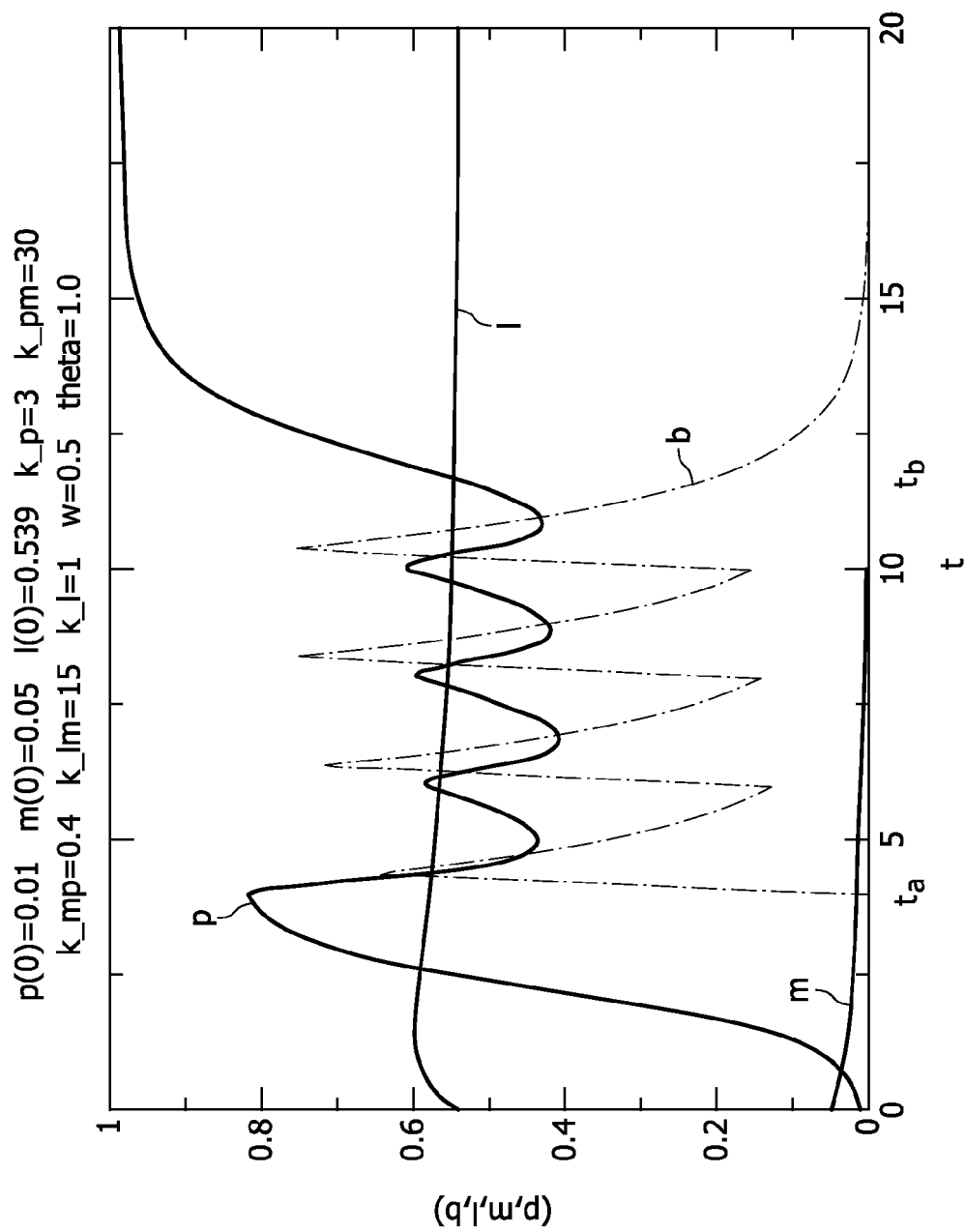
FIG. 5A-B show an example of an antibiotic therapy applied to the severe immuno-deficiency dynamic.
Figure 5B:
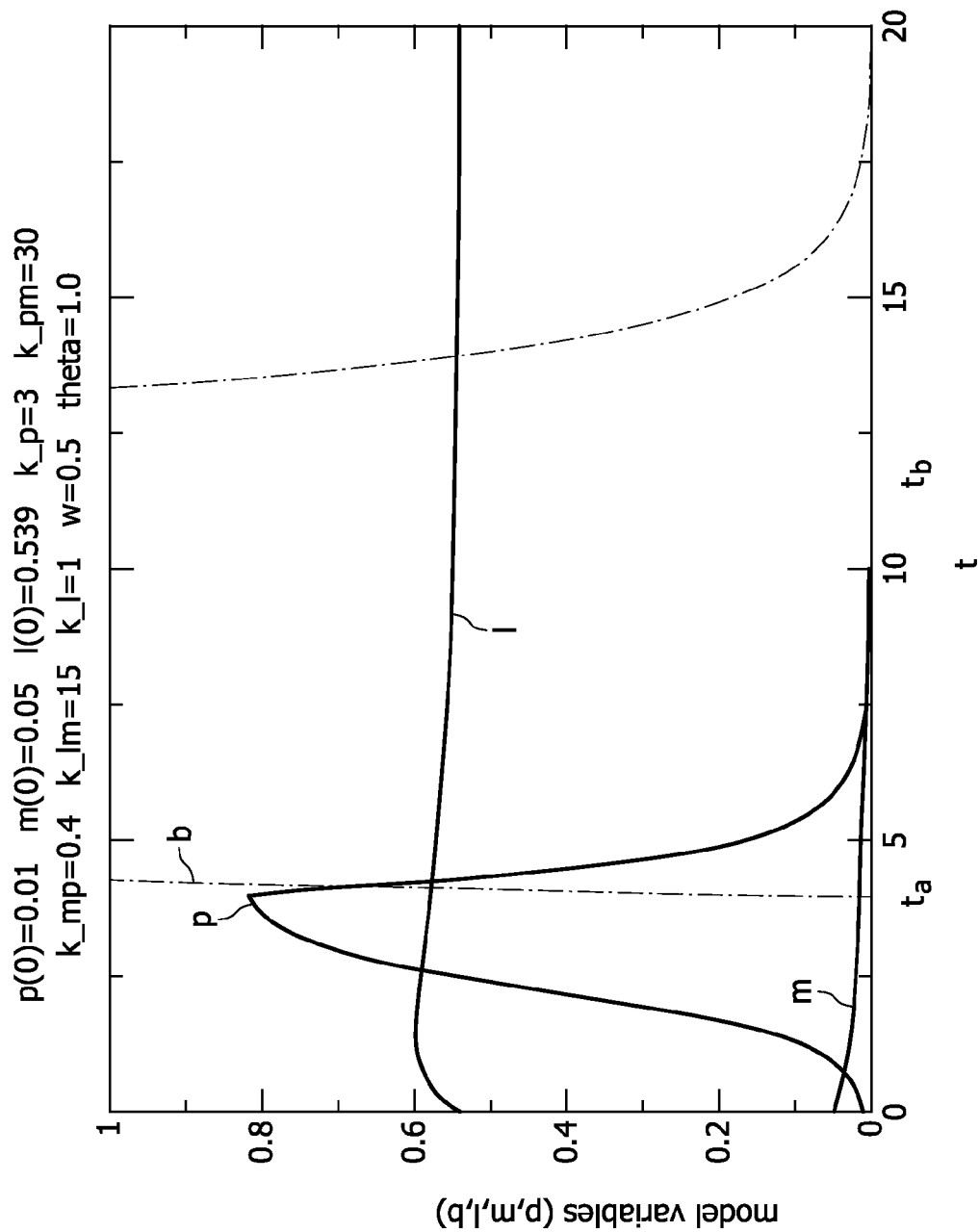
Figure 6A:
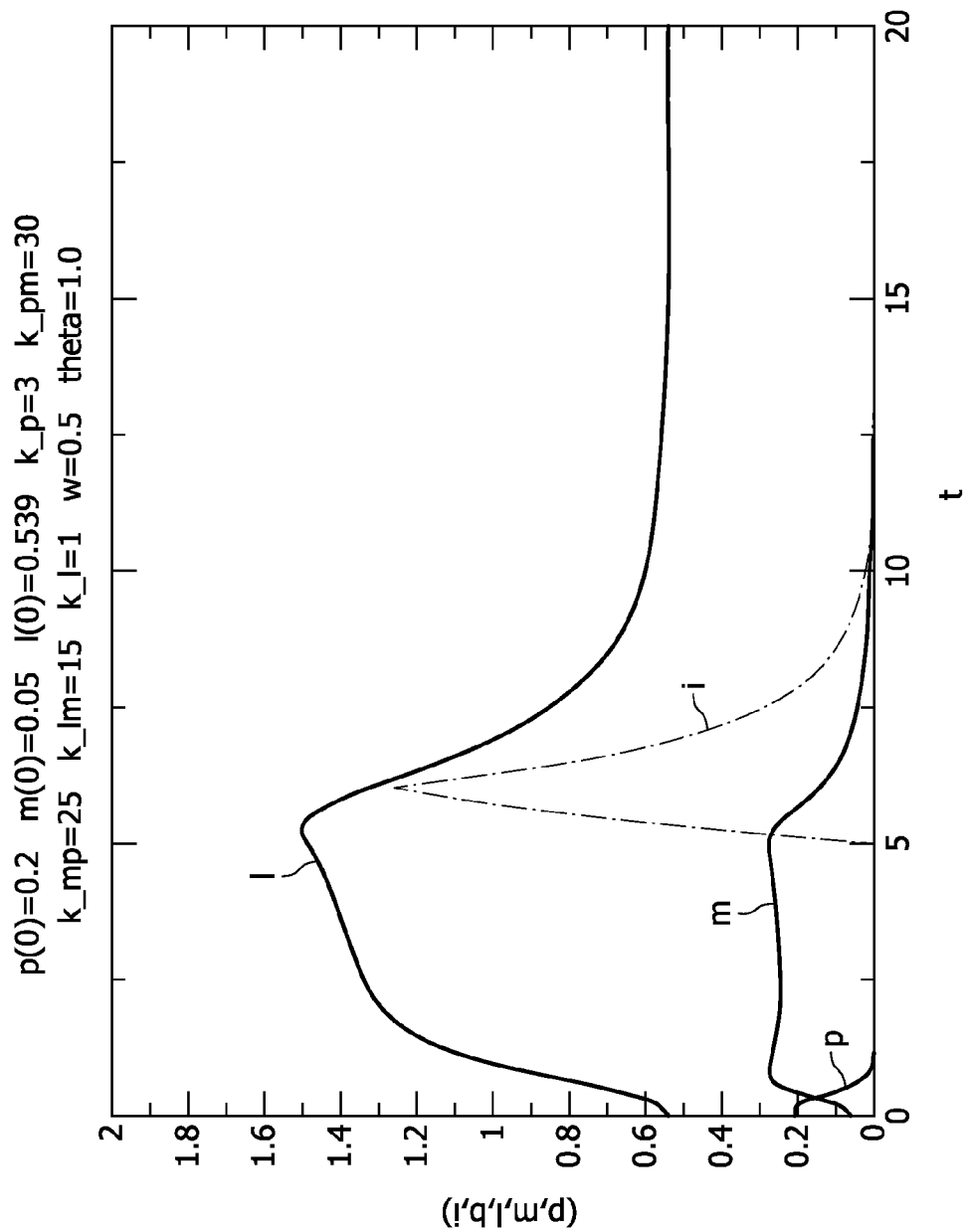
FIG. 6A-B show an example of anti-inflammatory therapy applied to the persistent non-infectious inflammation dynamic.
Figure 6B:
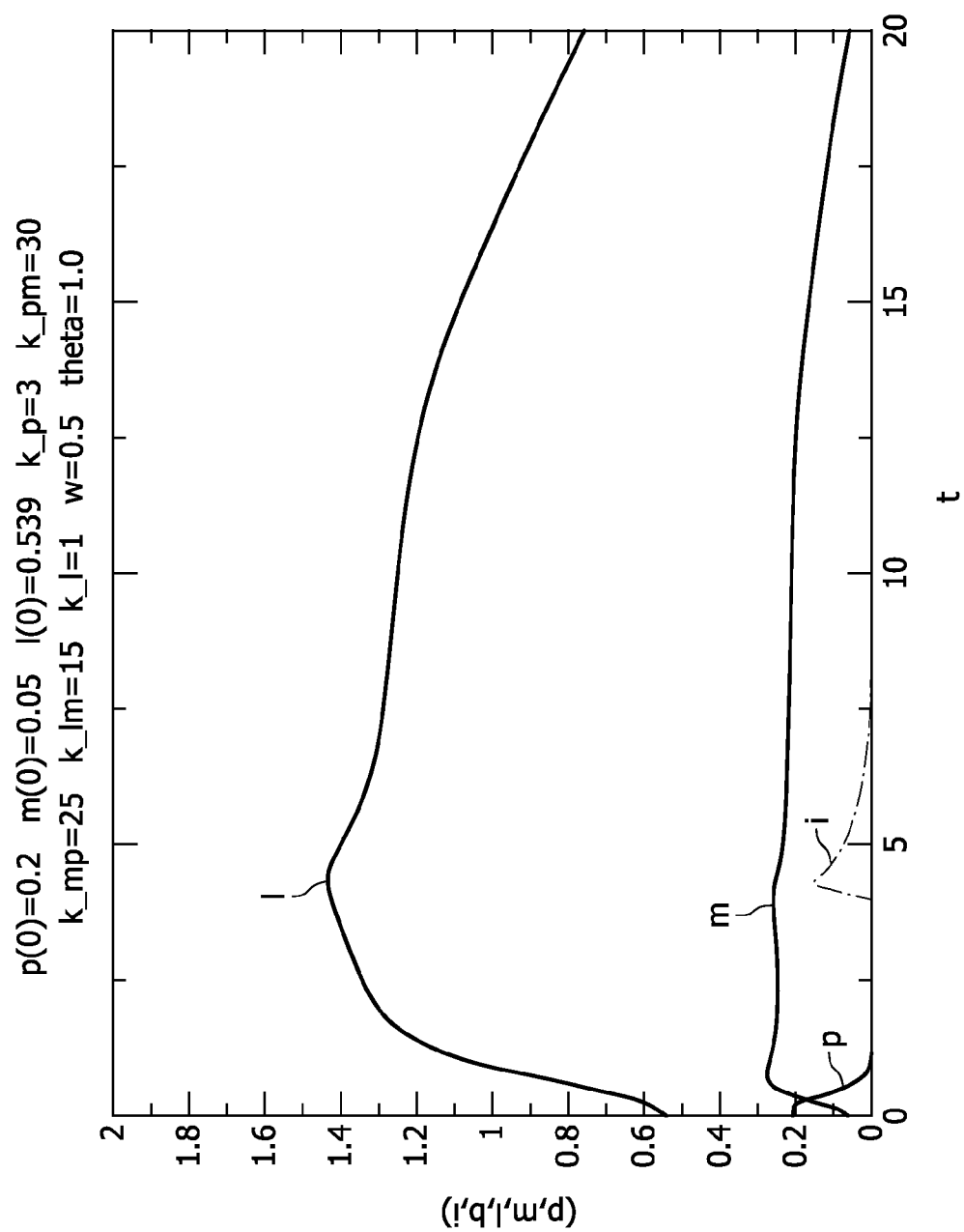

To illustrate how the extended model given by equations 4-9 may be used for assisting the clinician in choosing a suitable intervention, FIG. 5A-B show an example of an antibiotic therapy applied to the severe immuno-deficiency dynamic (shown in FIG. 2E) and FIG. 6A-B show an example of anti-inflammatory therapy applied to the persistent non-infectious inflammation dynamic (shown in FIG. 2B).

In the first scenario where the antibiotic therapy is applied, it is assumed that the rapid rise in the pathogen population in the immuno-deficient case was not noticed until hour 3. In this scenario, the pathogen has such a low $k_{mp}$ that it fails to trigger an immune response—the pathogen is referred to as a stealth pathogen.

Based on the mathematical model, the patient values inputted to the input device 100, the output device 104 of the medical apparatus 100 may in an embodiment show a prediction of patient values as shown in FIG. 2E. Based on this output, the clinician is assisted to decide among potential therapies. However, before actually executing this therapy, the clinician may want to test how this therapy affects the patient's patient values. Therefore, the medical apparatus 100 is configured for enabling the clinician to input values characterising the antibiotic therapy via the user input device 102.

Thus, the clinician may select a medication characterised by $k_{pb}=5$, $k_b=1$ and $c_b=1$ (derived from knowledge of the pathogen and the antiobiotic) and where the drug dosage data are specified by dose=2, period=2, duty=20, $t_a=4$ and $t_b=12$ is provided to the medical apparatus 100 either manually using the user input device 102 or electronically via a connection to an external apparatus such as a drug dosage apparatus.

The medical apparatus 100 generates an output, for example as shown in FIG. 5A, via the output device 104 providing the clinician with guidance for understanding the therapeutic effect of the potential medication.

FIG. 5A shows that the pathogen is affected, but not seriously. A second trial regimen increases the duty cycle to 100% and the dose to 4, corresponding to duty=100 and dose=4. As shown in FIG. 5B, this medication regimen is more effective.

The examples shown in FIGS. 5A and 5B shows the importance of choosing an efficient intervention. In this connection, an efficient intervention is dependent on drug dosage data (dose, period, duty, $t_a$ and $t_b$). Thus, by providing the clinician with the possibility of testing different values of drug dose and different values related to timing, that is, values of period and duty, and in particular the value of initiating the therapy given by $t_a$, allows the clinician to find the most efficient therapy.

In another example, a patient suffering from hyper-inflammation followed by immune collapse the timing of initiating ($t_a$) the anti-inflammatory therapy is known to be very important for the success of the therapy. Thus, by providing the clinician with the possibility of testing different timing strategies, by testing the therapeutic effect of different values of period, duty, $t_a$ and $t_b$, the risk of choosing a fatal start time $t_a$ is eliminated or at least reduced.

In the second scenario anti-inflammatory therapy is applied to the persistent non-infectious inflammation dynamic (shown in FIG. 2B). By applying the anti-inflammation therapy at hour 5 (after the pathogen has been defeated by the natural immune system) for one hour with $k_{mi}=2$, $k_i=1$, $c_i=1$, $period_i=1$, $dose=2$, $duty=100$, the desired outcome is achieved as shown in FIG. 6A. Being presented with the information shown in FIG. 6A, the clinician is assisted via the medical apparatus 100 to perform this hypothetical medication. However, from this presentation of patient values (p, m, l) and therapy value (i) the clinician may choose to adjust this dosing regimen for seeking a minimal regimen that achieves the desired damping of the hyperinflammation. To verify this new dosing regimen with dose=0.3 and duty=30, the relevant values are provided to the medical apparatus 100 which generates a test result similar to FIG. 6B. FIG. 6B shows that the adjusted dosing regimen is favourable to dosing regimen shown in FIG. 6A.

Other models than those described by equations 1-9 may be used with the medical apparatus 100. Thus, more complex models based on more variables (p, l, m, b, i) and parameters k may be used—for examples models involving 18 variables and 80 parameters may be used for creating more accurate estimations. The models may be based on differential equations, the models may include stochastic variable and the models may comprise statistical models.

Figure 7:
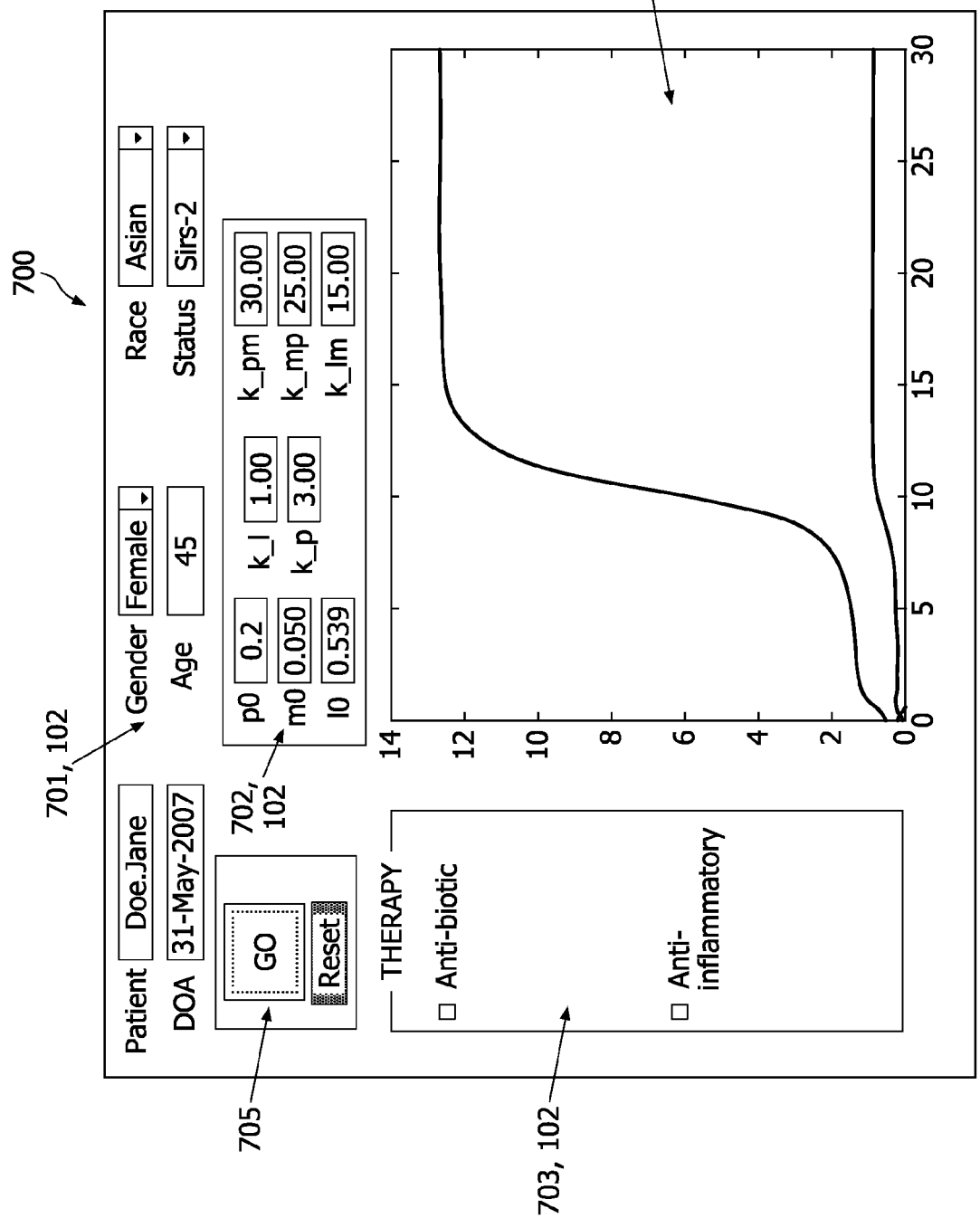
FIG. 7 shows an example of a user input device and an output device.

FIG. 7 shows an example of a user input device 701-703, 102 and an output device 704, 104—or to be more precise FIG. 7 shows the user interface 701-703 of an input device 102 and the user interface 704 of an output device 104, where the user interfaces 701-704 are combined into a single user interface 700. The user interface 700 furthermore comprises buttons 705 for starting the medical apparatus 100 to retrieve patient values from the input device 101 and the user input device 102, for starting adapting the model to the patient data and for starting generating output signals to the output device 104 for assisting the clinician in deciding a proper intervention. Accordingly, the user interface may be used in connection with the medical apparatus 100 by the clinician or other users for testing different interventions.

Graphs showing the predicted development of patient values and intended drug dosing regimens as shown in FIGS. 5-6 clearly are helpful tools for assisting the clinician in deciding what intervention should be executed, when it should be executed ($t_a$) and what the dosage period and duty should be (period, duty).

Accordingly, the output device 104 in connection with a user interface 704 is configured to output disease management information for assisting the clinician. By use of the predicted patient values various types of disease management information may be determined for example: suggestions for one or more interventions, timing data for assisting the clinician when to execute the intervention and estimates of confidence 1102 (FIG. 11) of the predicted patient values 1101 (FIG. 11) allowing the clinician to judge the reliability of the predictions.

Figure 8A:
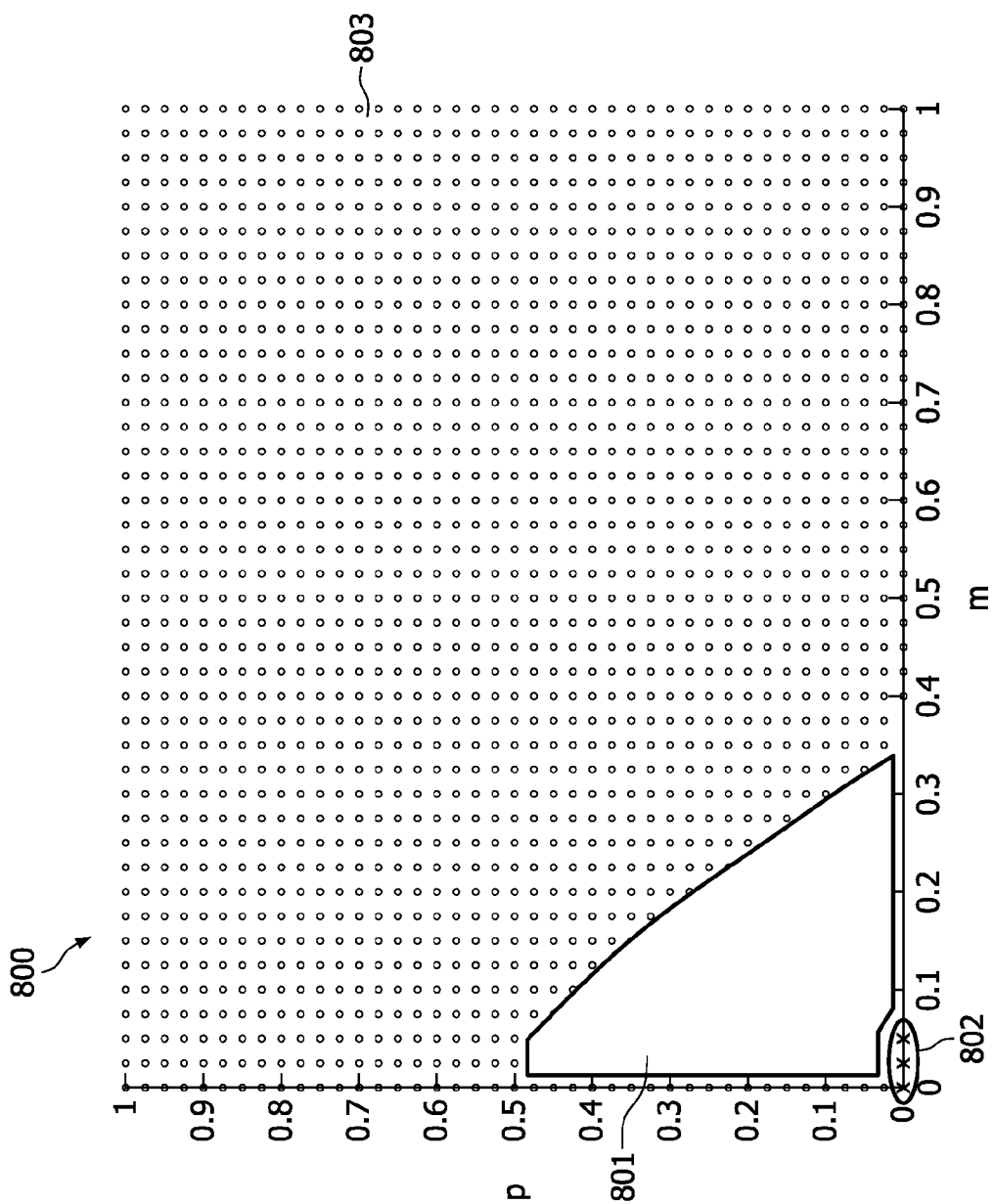
FIG. 8A shows a map of health regions of distinguishing health outcomes in model space.
Figure 8B:
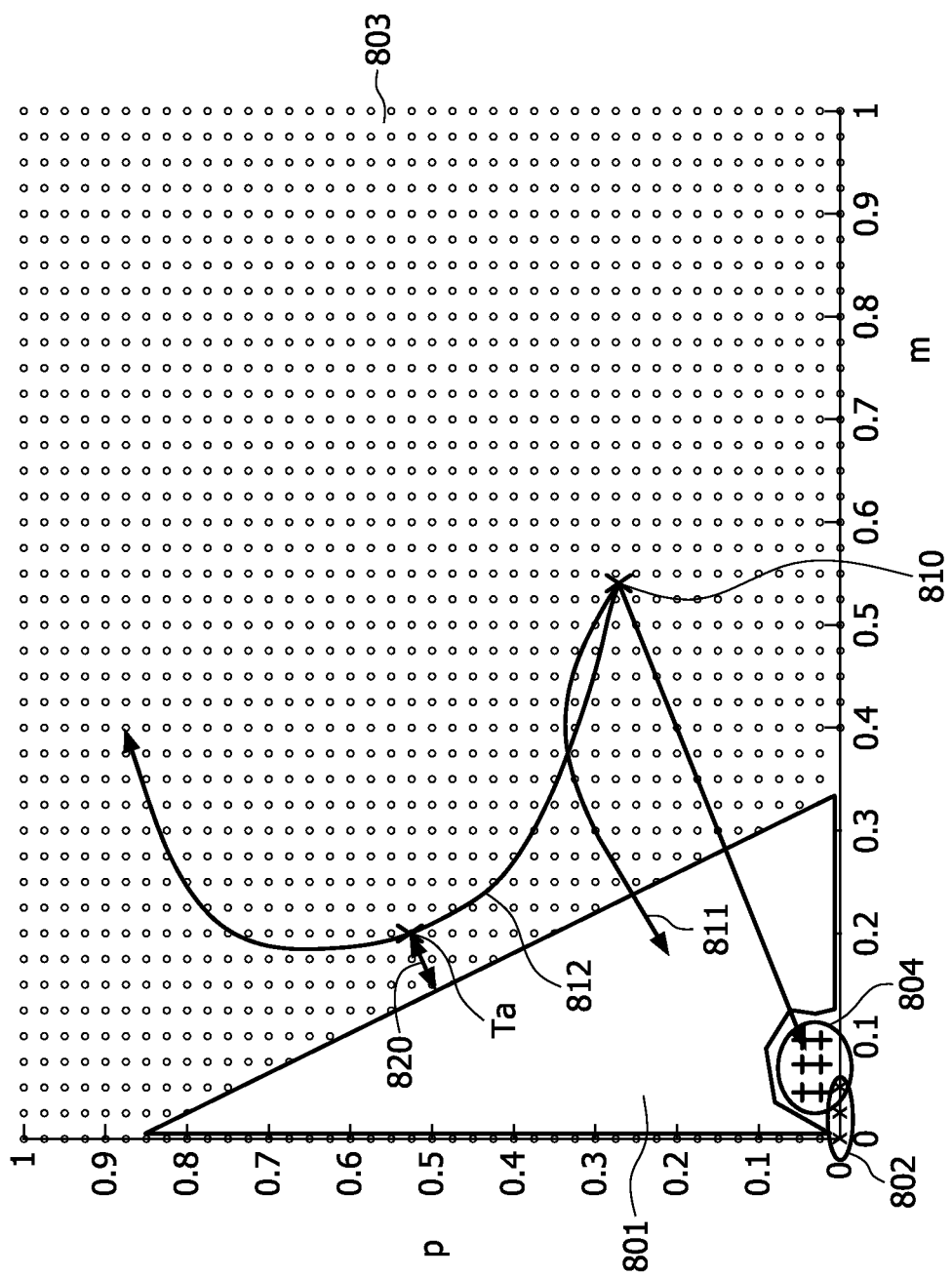
FIG. 8B shows the map of health regions using the same model as in FIG. 8A but with $k_{pm}$ increased from 30 to 40.

Furthermore, the output device 104 in connection with the user interface 704 is configured to output predicted patient trajectories (811-813), health regions (801-804) and interventions (820) as shown in FIG. 8A-B.

In an embodiment of the invention the computing device 103 could be used for analysis of the inputted patient values and therapy data of drug dosing regimens to provide the clinician with alternative or additional tools for assisting the clinician via the output device 104. Examples of such tools are shown in FIGS. 8A-B.

FIG. 8A shows a map 800 of health regions (801-803) of distinguishing health outcomes in model space (p, m) which has been determined by providing the adapted model (eg the model constituted by equations 1-3) with patient data (p, m and l), estimated k's and possibly also treatment data (b, i) for prediction of health outcomes.

For the particular example shown in FIGS. 8A-B, the map 800 has been determined by first equating the derivate of l to zero (setting equation 3 to zero) for creating a 2 dimensional p-m plane. Secondly, the space of initial conditions (p, m, l) is systematically scanned and from the initial conditions the model is used to derive the final health outcome. The final health outcomes are categorised according to distinct health definitions, for example the health dynamics of table 1: healthy response, persistent non-infectious inflammation, persistent infectious inflammation, recurrent infection and severe immuno-deficiency.

In the map shown in FIG. 8A distinct health outcomes 801-803 are indicated with different symbols, ie circles, dots, ect. Regions 801-803 of distinct health outcomes are also indicated. In FIG. 8A region 801 refers to desirable healthy responses (as shown in FIG. 2A), region 803 refers to persistent non-infectious inflammation (as shown in FIG. 2B) and region 802 refers to an untrusted region where the model is not capable of predicting patient values with sufficient reliability.

FIG. 8B shows the map of health regions 801-804 using the same model as in FIG. 8A but with $k_{pm}$ increased from 30 to 40 for modelling an increase in the effectiveness of the early inflammation at combating the pathogen. Due to the increase in $k_{pm}$ the region 801 of the healthy outcome has expanded and a new region 804 has appeared. Region 804 is an undesired region since initial conditions in this region lead to the recurrent infection dynamics as shown in FIG. 2D.

FIG. 8B shows how the map 800 of health regions can be used for assisting the clinician in managing the treatment of the patient by locating the patient's current patient values 810 in the map and determining patient trajectories 811-813 of patient health outcomes in model space (p, m) by providing the adapted model with treatment data for prediction of trajectories. In one scenario, trajectory 811 shows the health of the patient is predicted to develop into the healthy response region 801. In another scenario, trajectory 812 shows the disease of the patient is predicted to first develop towards the healthy response region 801, however, subsequently the disease of the patient will develop away from the healthy response region 801. In a third scenario the trajectory 813 predicts development of the disease into the undesired region of recurrent infection 804.

The different trajectories could have been caused by different interventions that are tested by the clinician using the user interface 700.

It is to be understood that maps 800 of models including more variables (p, l, m) than three variables, for example 5, 10 or 18 variables, may be visualised similarly to FIGS. 8A-B, for example by generating 3 or 4 two-dimensional maps 800 for visualising maps of a 5-variable model.

The health regions 801-804 and the patient trajectories 811-813 may be used by the clinician to decide what intervention should be applied. For example, if trajectory 811 in FIG. 88 represents the development of patient data (p, l, m) in response to a particular medication, that trajectory recommends the clinician to continue the planned medication, and continuing adapting the model to the current health of the patient on basis of the most recent patient data (p, l, m).

In another scenario, the patient trajectory 812 in FIG. 8B informs the clinician that at a given point in time Ta the patient data will approach the boundary of the healthy response region 801. The proximity 820 of the patient trajectory 812 at time Ta to the boundary of the healthy response region 801 can be used to suggest intervention strategies. Examples might be the application of antibiotics to shift p downward or anti-inflammatories to shift m down. This scenario shows in an embodiment of the invention how the medical apparatus 100 can assist the clinician in deciding what intervention would be beneficial to the patient and the time of the intervention—that is, the intervention must be initiated at time Ta for achieving the best efficiency, or possibly the intervention must be initiated before Ta so that the trajectory will veer into region at about Ta—like a spacecraft will apply a short engine reverse thrust before entering the earth's gravitational field so that is will be moving slowly enough to fall into this field. This example embodies in an example the disease management information comprising timing data.

Accordingly, in an embodiment, the map 800 of health regions, the patient trajectories, the boundaries or combinations thereof embodies outputting disease management information to an output device 104.

Figure 9:
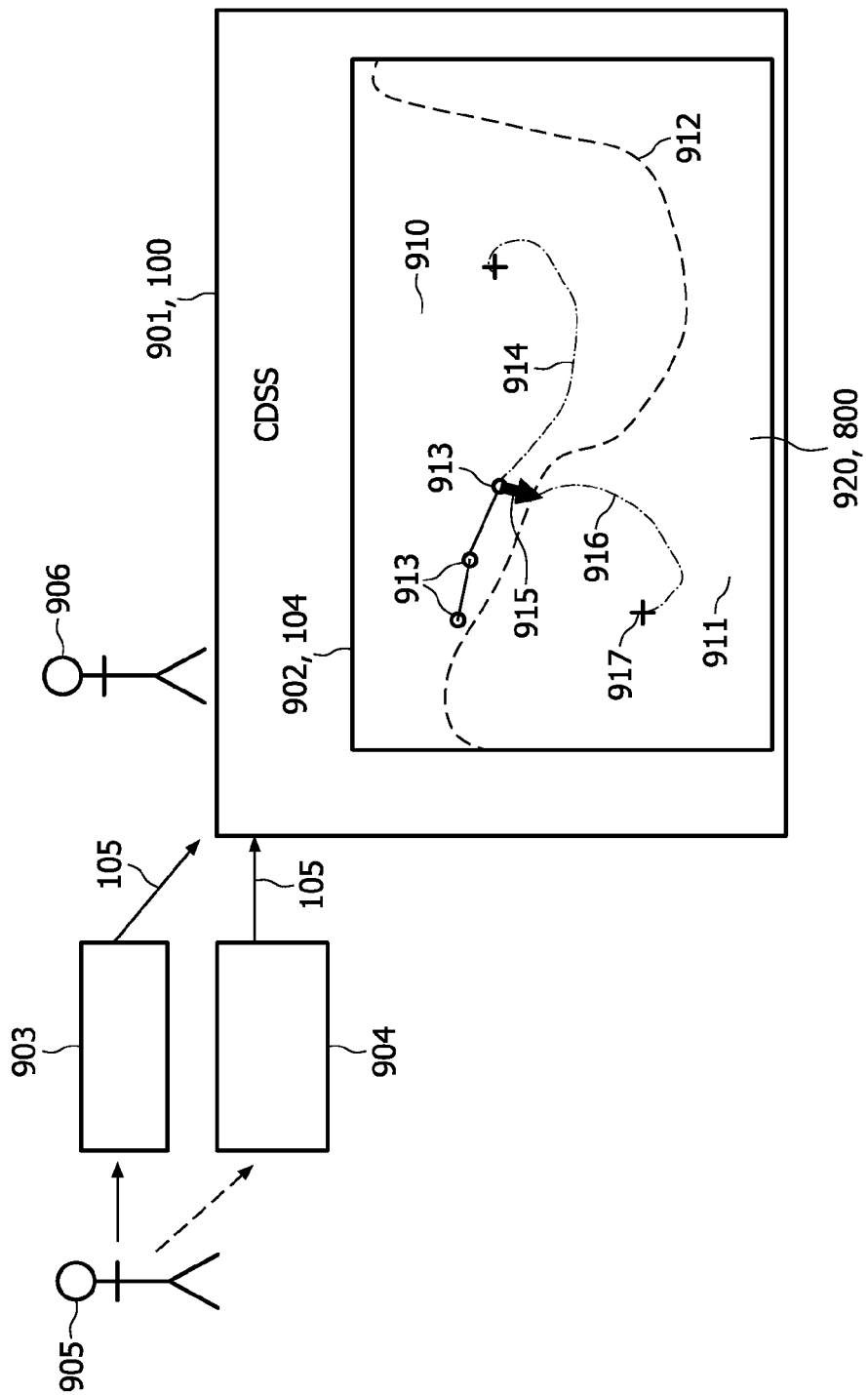
FIG. 9 shows an example of a medical apparatus comprising an output device.

FIG. 9 shows an example of a medical apparatus 901,100 comprising an output device 902,104. The medical apparatus 901 is provided with patient values comprising biological and physiological values via connections 105. The patient values may have been determined from biological analyser 903 and a physiological analyser 904 which have been provided with samples from the patient 905. Accordingly, the biological analyser 903 and a physiological analyser 904 are external apparatuses that provide patient values to the medical apparatus 901 via connections 105 or via the user input device 102.

The output device 902 shows a map 920 similar to the maps 800 shown in FIGS. 8A and 8B. The map 920 shows a healthy response region 911 and a non-healthy response region 910. The patient values of previous three samples are indicated as observations 913. By use of the model adapted to the patient 905, the predicted course 914 of the disease when no intervention is initiated is obtained by the computing device 103. In an embodiment of the invention the medical apparatus 901 may be capable of recommending intervention(s) that are likely to shift the patient's health into the healthy response region 911. The recommended intervention may be illustrated by arrow 915, and the therapeutic effect of the intervention is shown by the predicted course 916, which results in a stable healthy outcome 917.

The patient values provided to the input device 101 may be affected by noise or uncertainties, for example due to the measuring principles. Also, even small errors in the patient values used to set the initial conditions of the model or small errors in the estimated k-parameters ($k_p$, $k_{mp}$, $k_{lm}$) can lead to very different outcome predictions because of the non-linearities in the model.

In an embodiment of the invention, tolerances of the patient values are accounted for in an approach where all patient values and estimated rate constants (k-parameters) from the patient values are subjected some uncertainty. Knowledge of the inherent uncertainty of the measurement technologies can be used to specify two values, a high (above the provided value) and a low (below the provided value) that reasonable bracket the likely true value. A similar approach can be taken for the estimated rate constants, using other criteria, for instance the past history of previous estimates using fewer observations. For this illustration, we simply use a fixed percentage (1% down and 0.5% up) of the nominal values to produce these high/low pairs. Now we run the model for every combination of one of the three values (high, nominal, low) for each of the perturbed variables (for the model given by equations 4-9 there are 3 state variables (p, l, m) b=0 and i=0 with no uncertainty and 5 rate constants (k-parameters)). For each run of the model we keep track of the outer envelope of all computed trajectories.

Figure 11:
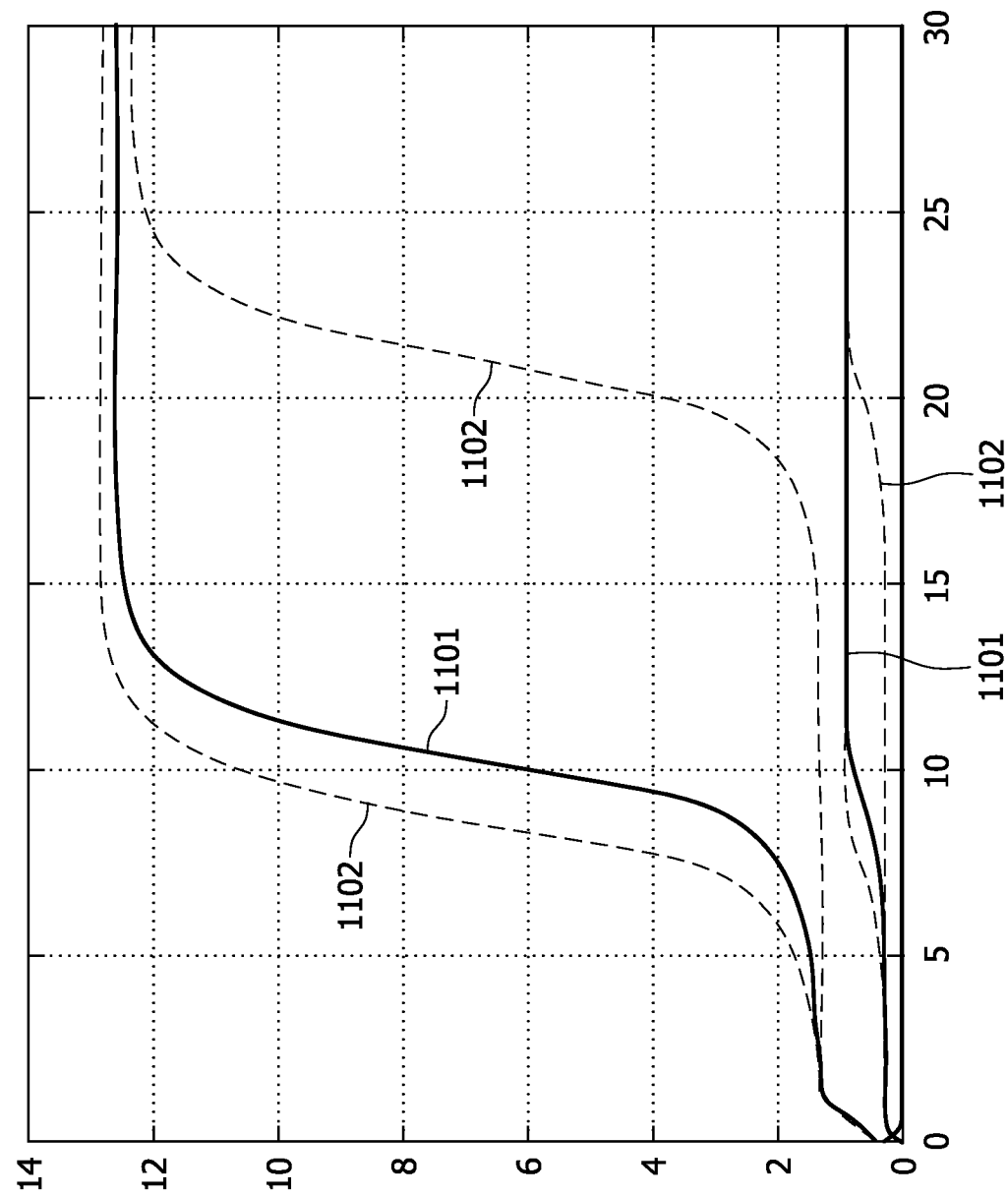
FIG. 11 shows predicted patient values combined with confidence envelopes.

Using this approach, the plots of the predicted trajectories 1101 may be augmented by plotting the upper and lower envelopes 1102 of the computed trajectories (dashed lines) as shown in FIG. 11. Here is such a plot for a hyper-inflammation case where the envelope indicates that the perturbations show bounded deviations from the nominal predictions.

The indications of this for the clinician are that while the timing of the onset and peak of the hyper-inflammation may be in some doubt, the occurrence is not (within the range of perturbations performed). Thus, providing estimates of confidence may advantageously provide clinicians with recommendations derived from these insights as to desirable therapies and their best scheduling.

Accordingly, disease management information provided to the output device 104 may in addition to showing predicted patient values 1101, show estimates of confidence 1102, for example in the form of envelopes 1102, so as to visualise the accuracy of the predicted patient values 1101.

Figure 10:
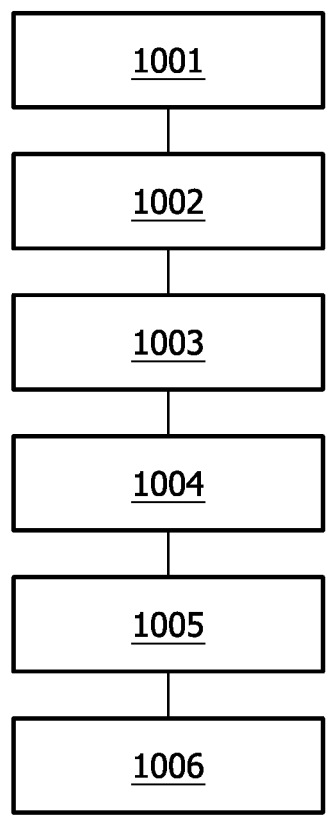
FIG. 10 shows the steps of a method according to an embodiment of the invention.

FIG. 10 shows the steps of a method according to an embodiment of the invention.

In step 1001, the medical apparatus 100 is provided with patient values via connections 105 to the input device 101 or the user input device 102.

In step 1002, the dynamic model is adapted to current dynamic of the patient by using a plurality of the patient values. In an example, adapting the model comprises estimating k-parameters. In an alternative embodiment, all patient values do not necessarily need to be used for adapting the model to the patient data. For example, extreme or untrustworthy patient values may be disregarded.

In optional step 1003, the course of the health of the patient when no interventions are performed is predicted using the adapted model by predicting future patient values. Optional step 1003 may be succeeded by outputting the predicted patient values to the output device 104.

In step 1004, the dynamic model is continuously adapted to the dynamic of the patient using recent patient values and using a plurality of the initial patient values for obtaining an improved model. The recent patient values have been provided to the medical apparatus subsequent to the initial patient values. It is understood that the dynamics model is re-adapted each time new patient values is provided to the input device 101 or the user input device 102. The continuous adaption continues as long as required.

In step 1005 predicted patient values are determined using the improved model (the most recent adapted model). The predicted patient values may optionally be used for determining the course of the health of the patient when no interventions are performed. Alternatively, the predicted patient values are determined using the improved model and therapy values (b, i) of interventions. The therapy values may be values from a medication which has already been executed, or the therapy values may be values of a medication which has not been executed but is tested on the medical apparatus 100 for predicting the therapeutic effect of a particular medication.

In step 1006 disease management information is outputted to the output device 104 of the medical apparatus 100 for assisting a clinician in managing the acute dynamic disease. The disease management information is determined from the predicted patient values.

The order of the steps 1001-1006 does not necessarily have to be the order illustrated and described, for example step 1006 may additionally be performed between optional step 1003 and step 1004.

In embodiments of the invention the medical apparatus can serve a number of users. Nurses can use the system to monitor current trends. It can aid clinicians by generating relevant output such as an alarm, a therapy plan, or an intervention recommendation. Furthermore, it can predict future patient trend based on current and hypothetical interventions. Additionally, hospital administrators can use an individual instance of the system or an aggregate of such systems to aid in scheduling resources (space, clinicians, equipment), inventory management, and quality assurance, to name a few.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A method for assisting a clinician in managing an acute dynamic disease of a patient, the method comprising
providing a medical apparatus which includes a computing device with initial patient values characterizing biological and/or physiological measures of the patient,
with the computing device, adapting a model of acute dynamics to dynamic of the patient using a plurality of the initial patient values provided to the medical apparatus,
continuing to provide recent patient values to the medical apparatus,
with the computing device, continuing adapting the model to the dynamic of the patient using the recent patient values and using a plurality of the initial patient values to improve the model, where said recent patient values have been provided to the medical apparatus subsequent to the initial patient values,
with the computing device, determining predicted patient values using the improved model,
outputting disease management information to an output device of the medical apparatus (100) for assisting the clinician in managing the acute dynamic disease, where the disease management information is determined from the predicted patient values.

2. The method according to claim 1, wherein the disease management information comprises an intervention, where the intervention is determined using the predicted patient values.

3. The method according to claim 2, further including;
(1) determining a trajectory of the predicted patient values, and (2) determining timing data for executing the intervention based on the trajectory of the predicted patient data approaching a healthy region boundary.

4. The method according to claim 1, wherein the disease management information comprises estimates of confidence of the predicted patient values.

5. The method according to claim 1, wherein the medical apparatus is configured for receiving therapy values of interventions including pharmacokinetics parameters, drug dose, and duty cycle of dosing and where the predicted patient values are determined using the improved model in connection with therapy values.

6. The method according to claim 1, wherein the method further comprises determining a sample time for providing the medical apparatus with the recent patient values obtained from biological and/or physiological analyses, wherein the sample time is determined from previously received initial and recent patient values.

7. The method according to claim 6, the sample time is determined based on at least one of frequency dynamics and a rate of change of the predicted patient values.

8. The method according to claim 1, wherein the method further comprises:
determining health regions which distinguish health outcomes in model space by providing the adapted model with patient data for prediction of health outcomes; and
determining patient trajectories of patient health outcomes in model space.

9. The method according to claim 8, further including:
determining a sampling time for providing the medical apparatus with the recent patient values based on proximity of the patient trajectory and the health region.

10. The method according to claim 1, wherein the output device is adapted for showing one or more disease management information selected from the list comprising predicted patient trajectories, health regions and interventions, for assisting the clinician.

11. The method according to claim 1, initial and recent patient values have an uncertainty range and wherein the output disease management information includes upper and lower values bracketing the predicted patient value.

12. The method according to claim 1, further including:
providing the medical apparatus with sets of therapy values including drug dose, dosing period, and duty cycle of dosing, and
generating a predicted patient values trajectory based on each set of therapy values to test the effect of the drug dose, the dosing period, and the duty cycle of dosing.

13. A medical apparatus for assisting a clinician in managing an acute dynamic disease of a patient, the medical apparatus comprising:
- an input device for receiving patient values characterizing biological and/or physiological measures of the patient; and
- a computing device for processing the patient values using a model of the acute dynamic disease, wherein:
- the input device is further configured to provide the computing device with initial patient values and a plurality of recent patient values provided subsequent to the initial patient values,
- the computing device is further configured for:
  - adapting the model to the initial patient values and the patient using a plurality of recent patient values, such that the model is continuingly adapted to dynamics of the patient,
  - determining predicted patient values using the adapting model,
- an output device configured to show disease management information for assisting the clinician in managing the acute dynamic disease, based on the predicted patient values predicted using the continuingly adapting model.

14. The medical apparatus according to claim 13, wherein the computing device is further configured for receiving therapy values indicative of interventions and the predicted patient values are determined using the continuingly adapted model and the received therapy values.

15. The medical apparatus according to claim 14, wherein the disease management information includes a predicted patient values trajectory and a healthy region boundary, and includes timing data for executing the intervention based on a relationship between the predicted patient values trajectory and the health region boundary.

16. The medical apparatus according to claim 15, wherein the computing device is further configured for:
- receiving sets of therapy values including drug dose, dosing period, and duty cycle of dosing, and
- generating a predicted patient values trajectory based on each set of therapy values to test the effect of the drug dose, the dosing period, and the duty cycle of dosing.

17. The medical apparatus according to claim 15, wherein the computing device is further configured for:
- determining a sampling time for providing the medical apparatus with the recent patient values based on proximity of the patient trajectory and the health region.

18. The medical apparatus according to claim 13, wherein the computing device is further configured for:
- determining a sampling time interval for providing the recent patient values based on at least one of frequency dynamics and a rate of change of the predicted patient values.

19. The medical apparatus according to claim 13, wherein there is uncertainty in the provided initial and recent patient values and wherein the output disease management information includes upper and lower values bracketing the predicted patient value.

20. A non-transitory computer readable medium carrying software configured for controlling a processor to;
- receive the medical apparatus with initial patient values,
- adapt a model of acute dynamic disease to dynamics of a patient using a plurality of the received initial patient values,
- continue to receive recent patient values,
- continue to adapt the model to the dynamics of the patient using the recent patient values and use the plurality of the initial patient values to improve the model, where said recent patient values are received subsequent to the initial patient values,
- determine predicted patient values using the improved model,
- output disease management information determined from the predicted patient values to an output device for assisting a clinician in managing an acute dynamic disease.

* * * * *